United States Patent

Gale et al.

[11] Patent Number: 5,635,203
[45] Date of Patent: Jun. 3, 1997

[54] TRANSDERMAL DEVICE HAVING DECREASED DELAMINATION

[75] Inventors: Robert M. Gale, Los Altos; Eun Soo Lee, Redwood City, both of Calif.

[73] Assignee: Alza Corporation, Palo Alto, Calif.

[21] Appl. No.: 315,043

[22] Filed: Sep. 29, 1994

[51] Int. Cl.$^6$ ............................................. A61F 13/00
[52] U.S. Cl. ........................ 424/448; 424/449; 602/41
[58] Field of Search ........................ 424/448, 449; 602/40

[56] References Cited

U.S. PATENT DOCUMENTS

| | | | |
|---|---|---|---|
| 4,144,317 | 3/1979 | Higuchi et al. | 424/21 |
| 4,542,013 | 9/1985 | Keith | 424/28 |
| 4,687,476 | 8/1987 | Pailin | 604/307 |
| 4,817,594 | 4/1989 | Juhasz | 128/155 |
| 4,904,475 | 2/1990 | Gale et al. | 424/449 |
| 4,915,950 | 4/1990 | Miranda et al. | 424/448 |
| 4,938,964 | 7/1990 | Sakai et al. | 424/443 |
| 5,217,718 | 6/1993 | Colley et al. | 424/449 |
| 5,298,258 | 3/1994 | Akemi et al. | 424/484 |
| 5,314,694 | 5/1994 | Gale | 424/448 |

*Primary Examiner*—D. Gabrielle Phelan
*Attorney, Agent, or Firm*—Michael J. Rafa; Steven F. Stone; Felissa H. Cagan

[57] ABSTRACT

A device for the transdermal administration of a drug comprising a microporous tie layer located between the drug reservoir and the contact adhesive. The tie layer eliminates blooming and delamination and has no appreciable adverse effect on either the drug flux or release rate from the device.

13 Claims, 2 Drawing Sheets

TRANSDERMAL DEVICE HAVING DECREASED DELAMINATION

FIELD OF INVENTION

This invention relates to medical devices for delivering drugs to the body through intact skin and more particularly to decreasing blooming and delamination at the interface of contact adhesive and drug reservoir layer of the medical device without affecting the drug flux and release rate from the therapeutic transdermal system.

BACKGROUND OF THE INVENTION

Devices that deliver drugs through skin for absorption into the body are known in the art. For example, U.S. Pat. No. 4,915,950 to Miranda et al, describes a transdermal drug delivery device including an absorbent source layer laminated to a pressure sensitive pharmaceutically acceptable contact adhesive. The source layer has an anchor adhesive layer laminated to its opposing side and a drug-impermeable backing layer applied to the anchor adhesive.

U.S. Pat. No. 4,817,594 to Juhasz, describes an integral anti-bacterial wound dressing containing the following five layers: the first layer of a permeable material; a layer of semipermeable material; a layer of electrically-conducted material in the form of an open mesh; a layer of charcoal fabric; and a non-adherent wound facing second layer of a permeable material.

U.S. Pat. No. 4,687,476 to Pailin, describes a continuous multi-layer strip used as a topical dressing, wherein the strip has a continuous layer of a first foil and on one side thereof a laminated material comprising a layer of skin adhesive protected with a release film.

U.S. Pat. No. 4,542,013 to Keith, describes a trinitroglycerol-containing substantially disaccharide-free polymeric diffusion matrix for transdermal systemic delivery of trinitroglycerol. The bandage may also include a facestock layer with skin adhesive, which comprises a foam, film-type, non-woven or vinyl tape with an acrylic, silicon or rubber adhesive.

U.S. Pat. No. 5,217,718 to Colley et al, describes a therapeutic system for the transdermal administration of dexmedetomidine that is a laminated composite of a backing layer, an optional anchor adhesive layer, a contact adhesive layer; and one or more additional layers. The composite also preferably contains an optional porous intermediate layer between the anchor and contact adhesive layer, wherein, when an anchor is included, it is typically an absorbent, non-woven fabric.

U.S. Pat. No. 5,298,258 to Akemi et al, describes an acrylic oily gel bioadhesive material comprising a substrate having on one surface thereof, a crosslinked gel layer.

U.S. Pat. No. 4,938,964 to Sakai et al, describes a formulation which may be applied using a conventional support. A cotton or non-woven fabric may be used for the support. (All of the aforementioned U.S. Patents are incorporated herein in their entirety by reference.)

U.S. Pat. No. 4,904,475 describes a porous support structure for use in a device for delivering ionized drugs from an aqueous reservoir.

In addition, Black "Transdermal Drug Delivery Systems", U.S. Pharmacist, November 1982, pp 49–78, provides additional background information regarding commercially available transdermal drug delivery systems. A reasonably complete summary of the factors involved in percutaneous absorbtion of drugs may be found in Arita, et al, "Studies on Percutaneous Absorption of Drugs", *Chem. Phar. Bull.*, Vol. 18, 1970, pp 1045–1049; Idson, "Percutaneous Absorption", *J. Phar. Sci.*, Vol. 64, No. 6, pp 910–922; and Clooney, *Advances in Biomedical Engineering*, Part I, Chapter 6, "Drug Permeation Through Skin: Controlled Delivery For Topical or Systemic Therapy", Marcel Dekker, Inc., New York and Basel, 1980, pp 305–318.

Although the transdermal drug delivery route is rapidly becoming a preferred delivery route for a wide variety of drugs, transdermal delivery is not without its problems. In general, direct contact of an adhesive with a drug reservoir which contains an amphipathic molecule, eg, a non-ionic surfactant such as a permeation enhancer, eg, a monoglyceride, ie, glycerol monolaurate or glycerol monooleate, has a problem of blooming at the interface of the contact adhesive/drug reservoir. The occurrence of blooming is caused by the surfactant migrating to the relatively lower energy interface generated by laminating an adhesive to the reservoir.

It is accordingly an objective of this invention to provide a drug delivery system adapted for use with drug reservoirs containing amphipathic molecules having reduced blooming and delamination at the interface of the contact adhesive and drug reservoir.

It is another object of the invention to provide a transdermal drug delivery device for use with an amphipathic molecule such as a non-ionic surfactant having a microporous tie layer interconnecting the drug reservoir and contact adhesive.

It is yet another object of the invention to provide a transdermal drug delivery device having a microporous tie layer interconnecting the drug reservoir and contact adhesive which does not affect the flux or the drug release profiles of the therapeutic transdermal system and which reduces the occurrence of blooming and delamination at the interface.

These and other objects and advantages of this invention will be readily apparent from the following description with reference to the accompanying figures.

DETAILED DESCRIPTION OF THE INVENTION

The specific drugs used herein are not critical to the invention. As used herein, the term "drug" is to be construed in its broadest sense as material which is intended to produce some beneficial effect on the organism to which it is applied.

As used herein, the term "transdermal" delivery or application refers to the delivery or application of agents by passage of skin, mucosa, and/or other body surfaces by topical application or by iontophoresis.

As used herein, the term "therapeutically effective" amount or rate refers to the amount or rate of drug or active agent needed to effect the desired therapeutic result.

As used herein "amphipathic" molecule refers to an unsymmetrical molecule having one end being hydrophilic and the other end hydrophobic, including, for example, non-ionic surfactants.

As used herein, the term "non-ionic surfactant" refers to a non-ionic agent which has the effect of altering the interfacial tension of water and other liquids or solids, for example, a monoglyceride. Surfactants may be used as a permeation enhancer for drug transport across skin.

As used herein, the term "monoglyceride" refers to glycerol monooleate, glycerol monolaurate, and glycerol monolinoleate, or a mixture thereof. Monoglycerides are generally available as a mixture of monoglycerides, with the mixture deriving its name from the monoglyceride present in the greatest amount.

As used herein, the term "glycerol monooleate" refers to glycerol monooleate itself or a mixture of glycerides wherein glycerol monooleate is present in the greatest amount.

As used herein, the term "glycerol monolaurate" refers to glycerol monolaurate itself or a mixture of glycerides wherein glycerol monolaurate is present in the greatest amount.

As used herein, the term "glycerol monolinoleate" refers to glycerol monolinoleate itself or a mixture of glycerides wherein glycerol monolinoleate is present in the greatest amount.

As used herein, the term "lactate ester" or "lactic ester of an alcohol" refers to ethyl lactate, lauryl lactate, myristyl lactate, cetyl lactate, or a mixture thereof.

Figure 1:
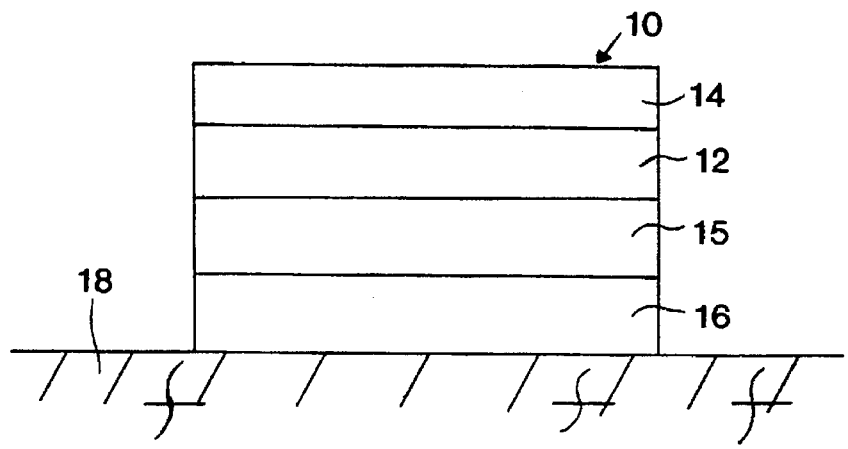
FIG. 1 is a cross-sectional view of one embodiment of the transdermal drug delivery system according to this invention.

Referring now to FIG. 1, a preferred embodiment of a transdermal delivery device 1, according to this invention is shown. The system is specifically adapted to reduce the problem of blooming and delamination of the contact adhesive from the drug reservoir layer when the drug reservoir contains a non-ionic surfactant. The inventors solved the problem by including a microporous tie layer between the drug reservoir layer and the contact adhesive. In FIG. 1, transdermal delivery device 10, comprises a reservoir containing a drug and the permeation enhancing mixture. Reservoir 12 is preferably in the form of a matrix containing the drug and permeation enhancer mixture dispersed therein. Reservoir 12 is sandwiched between a backing layer 14 and a microporous tie layer 15. On the other side of the tie layer 15 is the in-line contact adhesive layer 16. The device 10 adheres to the surface of the skin 18, by means of the adhesive layer 16. The adhesive layer 16 may optionally contain the permeation enhancing mixture and/or drug. A strippable release liner (not shown in FIG. 1) is normally provided along the exposed surface of the adhesive layer 16 as removed prior to application of device 10 to skin 18.

Figure 2:
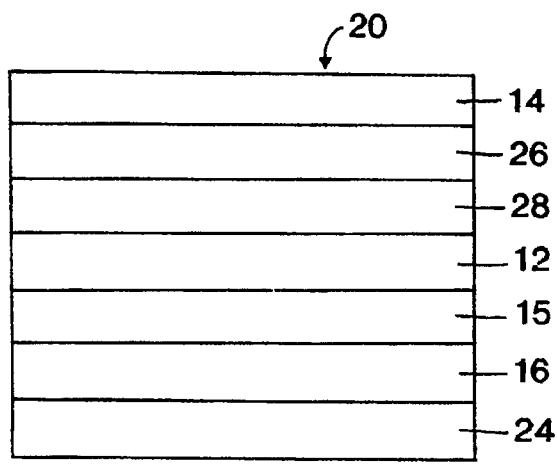
FIG. 2 is a cross-sectional view of another embodiment of the transdermal drug delivery system of this invention.

In FIG. 2, transdermal delivery device 20, comprises a drug- and permeation enhancing mixture-containing reservoir ("drug reservoir") 12 substantially as described with respect to FIG. 1. Permeation enhancer reservoir ("enhancer reservoir") 26 comprises the permeation enhancing mixture dispersed throughout and contains the drug at or below saturation. Enhancer reservoir 26 is made from substantially the same matrix as is used to form drug reservoir 12. Rate-controlling membrane 28 for controlling the release rate of the permeation enhancer from enhancer 26 to drug reservoir 12 is placed between the two reservoirs.

Superimposed over the permeation enhancer mixture 26 of device 20 is a backing 14. On the skin proximal side of reservoir 12 are a microporous tie layer 15; an adhesive layer 16, and a strippable liner 24 which would be removed prior to application of the device to the skin.

The purpose of the tie layer is to reduce blooming and delamination at the drug reservoir and contact adhesive but not to affect the flux or the release rate profiles of the drug from therapeutic transdermal systems. Potential tie layers should be formed from materials that have a low or negligible solubility of the amphipathic molecule and the drug and should have a porous or open structure so that the drug flux, as well as drug release rates, are not affected by the tie layer. Useful tie layers include but are not limited to microporous polypropylene membranes, microporous polyethylene membranes, porous polycarbonate, and spun bonded filamentous materials. The main defining characteristic of the tie layer is that it be formed of a material that does not absorb either the amphipathic molecule or the drug and is sufficiently open to allow transport of the drug and permeation enhancer.

The device is constructed so that the drug reservoir and/or adhesive layer when laminated on either side of the tie layer fills in the space defined by the open spaces in the tie layer.

In the embodiments of FIGS. 1 and 2, the carrier or matrix material of the reservoirs has sufficient viscosity to maintain its shape without oozing or flowing. If, however, the matrix or carrier is a low-viscosity flowable material such as a liquid or gel, the composition may be fully enclosed in a pouch or pocket as known to the art from U.S. Pat. No. 4,379,454, for example, and is illustrated in FIG. 3.

Figure 3:
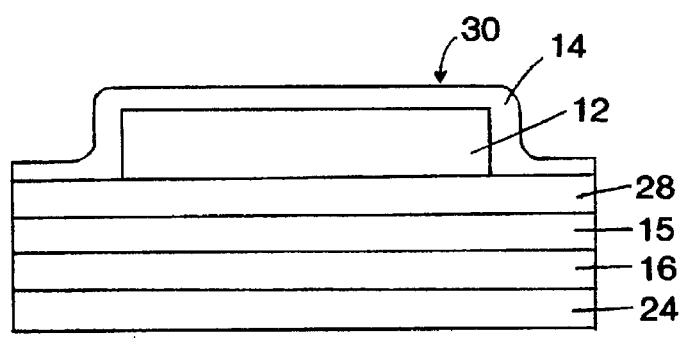
FIG. 3 is a cross-sectional view of still another embodiment of the transdermal drug delivery system according to this invention.

Device 30 in FIG. 3 comprises a backing member 14 which serves a protective cover for the device, in part structural support, and substantially keeps components in device 30 from escaping from the device. Device 30 also includes a reservoir 12 which contains the drug and permeation enhancer mixture and bears on its surface distant from the backing member 14, a rate-controlling membrane 28, for controlling the release of the drug and/or permeation enhancer mixture from device 30. The outer edges of the backing member overlay the edges of reservoir 12 and are joined along the parameter over the outer edges of the rate-controlling membrane 28 in a fluid-tight arrangement. This sealed reservoir may be effected by pressure, fusion, adhesion, and adhesive applied to the edges, or other methods known in the art. In this manner, reservoir 12 is contained only between backing member 14 and rate-controlling membrane 28. On the skin-proximal side of rate-controlling membrane 28 are a microporous tie layer 15; an adhesive layer 16; and a strippable liner 24, respectively. The strippable liner 24 would be removed prior to application of the device 30 to the skin.

In an alternative embodiment of device 30 of FIG. 3, reservoir 12, contains the permeation enhancing mixture and the drug at or below saturation. The drug at or above saturation and an additional amount of permeation enhancer mixture are present in the adhesive layer 16 which acts as a separate reservoir.

The formulation to be contained in a drug reservoir is non-aqueous based and designed to deliver the drug and permeation enhancer mixture at necessary fluxes. Typical non-aqueous gels are comprised of silicon fluid or mineral oil. Mineral oil-based gels also typically contain 1–2 wt % of a gelling agent such as colloidal silicon dioxide. The suitability of a particular gel depends upon the compatibility of its constituents with both the drug and permeation enhancing mixture and any other components in the formulation. The reservoir matrix should be compatible with the drug, permeation enhancer mixture, and any carrier therefore. The term "matrix" as used here refers to well-mixed composite ingredients fixed into shape.

When using a non-aqueous-based formulation, the reservoir matrix is preferably composed of a hydrophobic polymer. Suitable polymeric matrices are well known in the transdermal drug delivery art, and examples are listed in the above-named patents previously incorporated herein by reference. A typical laminated system would comprise a polymeric membrane and/or matrix such as ethylene vinyl acetate (EVA) copolymers, such as those described in U.S. Pat. No. 4,144,317, incorporated herein by reference preferably having a vinyl acetate (VA) content in the range of from about 9% up to about 60% and more preferably from about 9% to 40% VA. Polyisobutylene/oil polymers containing from 4–25% high molecular weight polyisobutylene and 20–81% low molecular weight polyisobutylene with the balance being an oil such as mineral oil or polyisobutenes may also be used in the matrix material.

The amount of drug present in the therapeutic device and required to achieve an effective therapeutic result depends on many factors, such as the minimum necessary dosage of the drug of the particular indication being treated; the solubility and permeability of the matrix, of the adhesive layer, and the rate-controlling membrane, if present; and the period of time for which the device will be fixed to the skin. The minimum amount of drug is determined by the requirement that sufficient quantities of drug must be present in the device to maintain the desired rate of release over the given period of application. The maximum amount for safety purposes is determined by the requirement that the quantity of drug present cannot exceed a rate of release that reaches toxic levels.

The drug is normally present in the matrix or carrier at a concentration in excess of saturation, the amount of excess being a function of the desired length of the drug delivery period of the system. The drug may, however, be present at a level below saturation without departing from this invention as long as the drug is continuously administered to the skin or mucosal site in an amount and for a period of time sufficient to provide the desired therapeutic rate.

The permeation enhancing mixture is dispersed throughout the matrix or carrier, preferably at a concentration sufficient to provide permeation-enhancing amounts of enhancer in the reservoir throughout the anticipated administration period. Where there is an additional, separate permeation enhancer matrix layer as well, as in FIG. 3, the permeation enhancer normally is present in the separate reservoir in excess of saturation.

In addition to the drug and permeation enhancer mixture, which are essential to the invention, the matrix or carrier may also contain dies, pigments, inert fillers, excipients, and other conventional components of pharmaceutical products for transdermal devices known in the art.

Because of the wide variation in skin permeability from individual to individual and from site to site on the same body, it may be preferable that the drug and permeation enhancer mixture be administered from a rate-controlled transdermal delivery device. Rate control can be obtained through either an adhesive or through other means. A certain amount of drug will bind reversibly to the skin, and is accordingly preferred that the skin-contacting layer of the device include this amount of the agent as a loading dose.

The surface area of the device of this invention can vary from less than 1 cm$^2$ to greater than 200 cm$^2$. A typical device, however, will have a surface area within the range of about 5–50 cm$^2$.

The devices of this invention can be designed to effectively deliver drug for an extended period of time from several hours up to seven days or longer. Seven days is generally the maximum time limit for application of a single device because the adverse effect of inclusion of a skin site increases with time and a normal cycle of sloughing and replacement of the skin cells occurs in about seven days.

It is believed that this invention has utility in connection with the delivery of drugs within the broad class normally delivered through body surfaces and membranes, including skin. As used herein, the expressions "drug" and "agent" are used interchangeably and are intended to have their broadest interpretation as to any therapeutically active substance which is delivered to a living organism to produce a desired, usually beneficial, effect. In general, this includes therapeutic agents in all of the major therapeutic areas, including, but not limited to, ACE inhibitors, adenohypophyseal hormones, adrenergic neuron blocking agents, adrenocortical steroids, inhibitors of the biosynthesis of adrenocortical steroids, alpha-adrenergic agonists, alpha-adrenergic antagonists, selective alpha-two-adrenergic agonists, analgesics, antipyretics and anti-inflammatory agents, androgens, local anesthetics, general anesthetics, antiaddictive agents, antiandrogens, antiarrhythmic agents, antiasthmatic agents, anticholinergic agents, anticholinesterase agents, anticoagulants, antidiabetic agents, antidiarrheal agents, antidiuretic, antiemetic and prokinetic agents, antiepileptic agents, antiestrogens, antifungal agents, antihypertensive agents, antimicrobial agents, antimigraine agents, antimuscarinic agents, antineoplastic agents, antiparasitic agents, antiparkinson's agents, antiplatelet agents, antiprogestins, antithyroid agents, antitussives, antiviral agents, atypical antidepressants, azaspirodecanediones, barbiturates, benzodiazepines, benzothiadiazides, beta-adrenergic agonists, beta-adrenergic antagonists, selective beta-one-adrenergic antagonists, selective beta-two-adrenergic agonists, bile salts, agents affecting volume and composition of body fluids, butyrophenones, agents affecting calcification, calcium channel blockers, cardiovascular drugs, catecholamines and sympathomimetic drugs, cholinergic agonists, cholinesterase reactivators, dermatological agents, diphenylbutylpiperidines, diuretics, ergot alkaloids, estrogens, ganglionic blocking agents, ganglionic stimulating agents, hydantoins, agents for control of gastric acidity and treatment of peptic ulcers, hematopoietic agents, histamines, histamine antagonists, 5-hydroxytryptamine antagonists, drugs for the treatment of hyperlipoproteinemia, hypnotics and sedatives, immunosuppressive agents, laxatives, methylxanthines, monoamine oxidase inhibitors, neuromuscular blocking agents, organic nitrates, opioid analgesics and antagonists, pancreatic enzymes, phenothiazines, progestins, prostaglandins, agents for the treatment of psychiatric disorders, retinoids, sodium channel blockers, agents for spasticity and acute muscle spasms, succinimides, thioxanthenes, thrombolytic agents, thyroid agents, tricyclic antidepressants, inhibitors of tubular transport of organic compounds, drugs affecting uterine motility, vasodilators, vitamins and the like.

Representative drugs include, by way of example and not for purposes of limitation, bepridil, diltiazem, felodipine, isradipine, nicardipine, nifedipine, nimodipine, nitredipine, verapamil, dobutamine, isoproterenol, carteolol, labetalol, levobunolol, nadolol, penbutolol, pindolol, propranolol, sotalol, timolol, acebutolol, atenolol, betaxolol, esmolol, metoprolol, albuterol, bitolterol, isoetharine, metaproterenol, pirbuterol, ritodrine, terbutaline, alclometasone, aldosterone, amcinonide, beclomethasone dipropionate, betamethasone, clobetasol, clocortolone, cortisol, cortisone, corticosterone, desonide, desoximetasone, 11-desoxycorticosterone, 11-desoxycortisol, dexamethasone, diflorasone, fludrocortisone, flunisolide, fluocinolone, fluocinonide, fluorometholone, flurandrenolide, halcinonide, hydrocortisone, medrysone, 6α-methylprednisolone, mometasone, paramethasone, prednisolone, prednisone, tetrahydrocortisol, triamcinolone, benoxinate, benzocaine, bupivacaine, chloroprocaine, cocaine, dibucaine, dyclonine, etidocaine, lidocaine, mepivacaine, pramoxine, prilocaine, procaine, proparacaine, tetracaine, alfentanil, chloroform, clonidine, cyclopropane, desflurane, diethyl ether, droperidol, enflurane, etomidate, fentanyl, halothane, isoflurane, ketamine hydrochloride, meperidine, methohexital, methoxyflurane, morphine, propofol, sevoflurane, sufentanil, thiamylal, thiopental, acetaminophen, allopurinol, apazone, aspirin, auranofin, aurothioglucose, colchicine, diclofenac, diflunisal, etodolac, fenoprofen, flurbiprofen, gold sodium thiomalate, ibuprofen, indomethacin, ketoprofen, meclofenamate, mefenamic acid, mesalamine, methyl salicylate, nabumetone, naproxen, oxyphenbutazone, phenacetin, phenylbutazone, piroxicam, salicylamide, salicylate, salicylic acid, salsalate, sulfasalazine, sulindac, tolmetin, acetophenazine, chlorpromazine, fluphenazine, mesoridazine, perphenazine, thioridazine, trifluoperazine, triflupromazine, disopyramide, encainide, flecainide, indecainide, mexiletine, moricizine, phenytoin, procainamide, propafenone, quinidine, tocainide, cisapride, domperidone, dronabinol, haloperidol, metoclopramide, nabilone, prochlorperazine, promethazine, thiethylperazine, trimethobenzamide, buprenorphine, butorphanol, codeine, dezocine, diphenoxylate, drocode, hydrocodone, hydromorphone, levallorphan, levorphanol, loperamide, meptazinol, methadone, nalbuphine, nalmefene, nalorphine, naloxone, naltrexone, oxybutynin, oxycodone, oxymorphone, pentazocine, propoxyphene, isosorbide dinitrate, nitroglycerin, theophylline, phenylephrine, ephedrine, pilocarpine, furosemide, tetracycline, chlorpheniramine, ketorolac, bromocriptine, guanabenz, prazosin, doxazosin, and flufenamic acid.

Other representative drugs include benzodiazepines, such as alprazolam, brotizolam, chlordiazepoxide, clobazam, clonazepam, clorazepate, demoxepam, diazepam, flumazenil, flurazepam, halazepam, lorazepam, midazolam, nitrazepam, nordazepam, oxazepam, prazepam, quazepam, temazepam, triazolam, and the like; an antimuscarinic agents, such as anisotropine, atropine, clidinium, cyclopentolate, dicyclomine, flavoxate, glycopyrrolate, hexocyclium, homatropine, ipratropium, isopropamide, mepenzolate, methantheline, oxyphencyclimine, pirenzepine, propantheline, scopolamine, telenzepine, tridihexethyl, tropicamide, and the like; an estrogen such as chlorotrianisene, diethylstilbestrol, estradiol, estradiol cypionate, estradiol valerate, estrone, estrone sodium sulfate, estropipate, ethinyl estradiol, mestranol, quinestrol, sodium equilin sulfate and the like; an androgen, such as danazol, fluoxymesterone, methandrostenolone, methyltestosterone, nandrolone decanoate, nandrolone phenpropionate, oxandrolone, oxymetholone, stanozolol, testolactone, testosterone, testosterone cypionate, testosterone enanthate, testosterone propionate, and the like; or a progestin such as ethynodiol diacetate, gestodene, hydroxyprogesterone caproate, levonorgestrel, medroxyprogesterone acetate, megestrol acetate, norethindrone, norethindrone acetate, norethynodrel, norgestrel, progesterone, and the like.

Preferably, the transdermal drug delivery device contains a sufficient amount of permeation enhancer mixture to provide systemic administration of the drug through the skin for a predetermined period of time for the drug to provide an effective therapeutic result.

The aforementioned patents describe a wide variety of materials which can be used for fabricating the various layers and components of the transdermal drug delivery devices according to this invention. This invention, therefore, contemplates the use of materials other than those specifically disclosed herein, including those which may hereafter become known to the art and to be capable of performing the necessary functions.

The following example is offered to illustrate the practice of the present invention and is not intended to limit the invention in any manner.

EXAMPLE 1

The drug/permeation enhancer reservoir was prepared by mixing ethylene vinyl acetate copolymer having a vinyl acetate content of 40 percent ("EVA 40", U.S.I. Chemicals, Illinois) in an internal mixer (Bra Bender type mixer) until the EVA 40 pellets fused. Testosterone, glycerol monolaurate, lactic acid, myristyl lactate, lauroyl lactylic acid, and lauryl lactate were then added as required. The mixture was blended, cooled and calendered to a 5 mil thick film. The compositions of the reservoirs are given in Table 1.

TABLE 1

Figure 4:
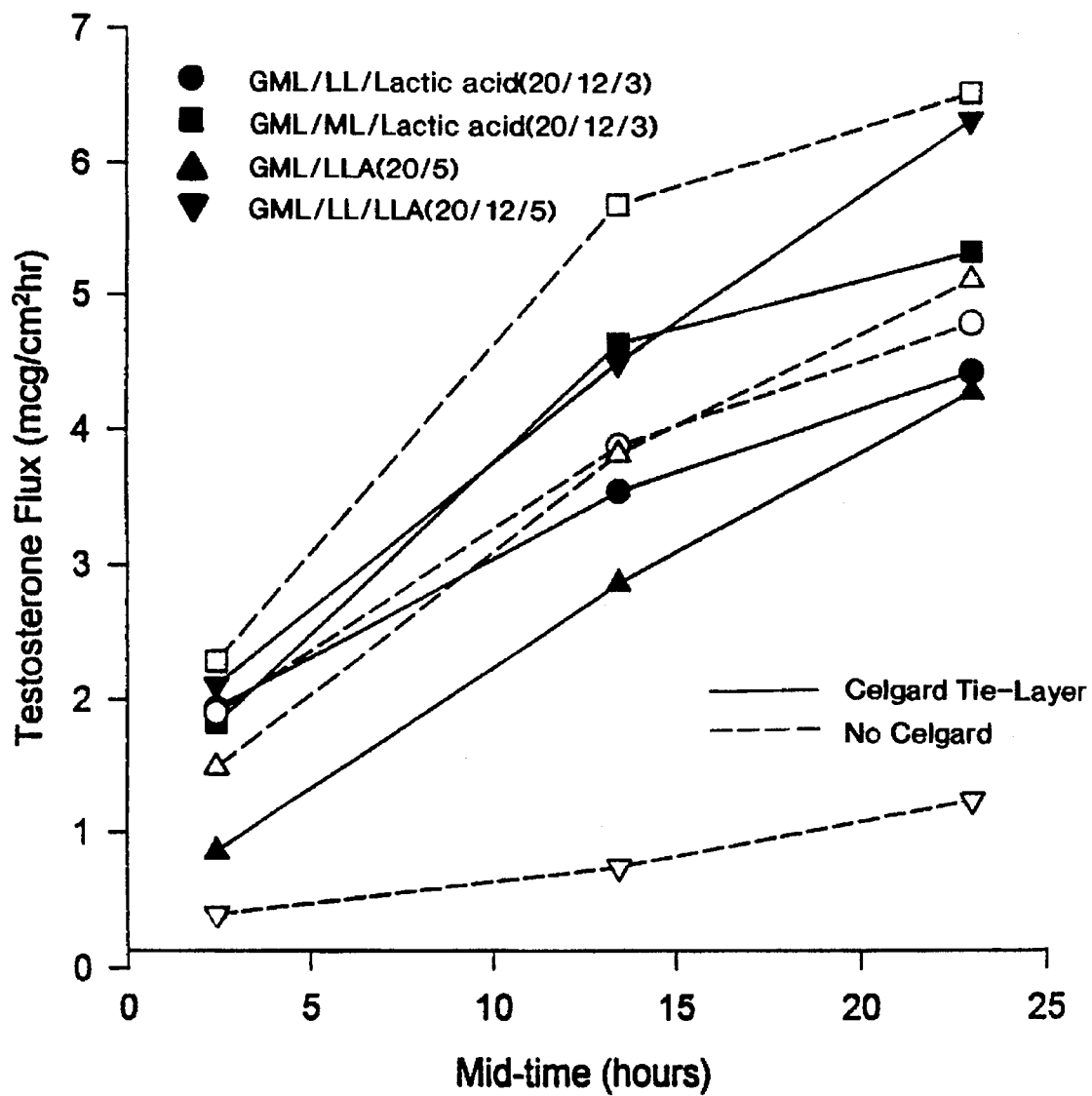
FIG. 4 is a graph of the effect of a microporous tie layer on the flux of testosterone at 35° C., in vitro.

Drug/Permeation Enhancer Reservoir Composition
(weight percent)
FIG. 4

GML/lauryl lactate/lactic acid/testosterone/EVA 40
20/12/3/10/55
GML/myristyl lactate/lactic acid/testosterone/EVA 40
20/12/3/10/55
GML/lauroyl lactylic acid/testosterone/EVA 40
20/5/10/65
GML/lauryl lactate/lauroyl lactylic acid/testosterone/EVA 40
20/12/5/10/53

This film was then laminated to an acrylic contact adhesive (MSP041991 P, 3M) on one side and Medpar® backing (3M) on the opposite side. All systems were tested with and without a Celgard® (Hoechst Celanese) microporous polypropylene membrane which, when present, was laminated between the reservoir and adhesive. The laminate was then cut into 1.98 cm$^2$ circles using a stainless steel punch.

Circular pieces of human-epidermis were mounted on horizontal permeation cells with the stratum corneum facing the donor compartment of the cell. The release liner of the system was then removed and the system was centered over the stratum corneum side of the epidermis. The cells were then masked. A known volume of the receptor solution (0.10% phenol/H$_2$O) that had been equilibrated at 35° C. was placed in the receptor compartment. Air bubbles were removed; the cell was capped and placed in a water bathshaker at 35° C.

At given time intervals, the entire receptor solution was removed from the cells and replaced with an equal volume of fresh receptor solutions previously equilibrated at 35° C. The receptor solutions were stored in capped vials at 4° C. until assayed for testosterone content by HPLC.

The fluxes achieved for the different systems are shown in FIG. 4. As shown in FIG. 4, the fluxes for the devices that contained the Celgard® were equivalent on average to those fluxes obtained from the devices that did not contain the Celgard® membrane.

No blooming or delamination was observed.

The invention has been described in detail with particular reference to certain preferred embodiments thereof, but it will be understood that variations and modifications can be affected within the scope and spirit of the invention.

What is claimed is:

1. A transdermal device including a non-aqueous reservoir containing a drug and a non-ionic surfactant for the transdermal administration of a drug at a therapeutically effective rate, which device comprises:
   a) a non-aqueous reservoir comprising a therapeutically effective amount of a drug and a skin permeation-enhancing amount of a non-ionic surfactant;
   b) a non-rate controlling tie layer on the skin-proximal surface of the reservoir that is formed from a material having low or negligible solubility for the non-ionic surfactant and the drug and is sufficiently porous so as not to affect, to a rate-controlling extent, the drug flux or drug release rate from the device;
   c) a backing on the skin-distal surface of the reservoir; and
   d) means for maintaining the reservoir in drug- and permeation enhancer mixture-transmitting relation with the skin on the skin-proximal surface of the tie layer.

2. A transdermal device including a non-aqueous reservoir containing a drug and a non-ionic surfactant for the transdermal administration of a drug at a therapeutically effective rate, which device comprises:
   a) a non-aqueous first reservoir comprising a therapeutically effective amount of a drug and a non-ionic surfactant skin permeation enhancer;
   b) a second non-aqueous reservoir comprising drug at or below saturation and an excess of the non-ionic surfactant permeation enhancer;
   a rate-controlling membrane between the first and second reservoir;
   d) a backing on the skin-distal surface of the second reservoir;
   e) a non-rate controlling tie layer on the skin proximal surface of the first reservoir that is formed from a material having low or negligible solubility for the non-ionic surfactant and the drug and is sufficiently porous so as not to affect, to a rate-controlling extent, the drug flux or drug release rate from the device; and
   f) means for maintaining the first and second reservoirs in drug- and permeation enhancer mixture-transmitting relation with the skin on the skin-proximal surface of the tie layer.

3. A device according to claim 1 or 2 wherein the permeation enhancer mixture comprises a monoglyceride or mixture of monoglycerides.

4. A device according to claim 3 wherein the permeation enhancer mixture additionally comprises a lactic ester or mixture of lactic esters.

5. A device according to claim 3 or 4 wherein the monoglyceride is glycerol monolaurate.

6. A device according to claim 5 wherein the lactic ester is lauryl lactate.

7. A device according to claim 4 wherein the monoglyceride is glycerol monolaurate and the lactic ester is ethyl lactate or lauryl lactate or a mixture thereof.

8. A device according to claim 1 or 2 wherein the tie layer is microporous polypropylene.

9. The device according to claim 1 or 2 wherein the tie layer is microporous polyethylene.

10. The device according to claim 7 wherein the tie layer is microporous polypropylene.

11. The device according to claim 8 wherein the drug is testosterone.

12. The device according to claim 8 wherein the drug is alprazolam.

13. The device according to claim 8 wherein the drug is ketorolac.

* * * * *